(12) United States Patent
Harding

(10) Patent No.: US 7,527,716 B2
(45) Date of Patent: May 5, 2009

(54) CONNECTOR CONFIGURATION FOR ELECTROCHEMICAL CELLS AND METERS FOR USE IN COMBINATION THEREWITH

(75) Inventor: Ian Harding, Somerville, MA (US)

(73) Assignee: Agamatrix, Inc., Salem, NH (US)

( * ) Notice: Subject to any disclaimer, the term of this patent is extended or adjusted under 35 U.S.C. 154(b) by 599 days.

(21) Appl. No.: 10/908,662

(22) Filed: May 21, 2005

(65) Prior Publication Data

US 2005/0258050 A1 Nov. 24, 2005

Related U.S. Application Data

(60) Provisional application No. 60/521,555, filed on May 21, 2004.

(51) Int. Cl.
*G01N 33/487* (2006.01)

(52) U.S. Cl. .......................... 204/403.02; 204/403.01; 204/403.03; 204/403.04; 205/777.5; 205/778

(58) Field of Classification Search ......... 204/400–435; 205/777.5–778
See application file for complete search history.

(56) References Cited

U.S. PATENT DOCUMENTS

| | | | |
|---|---|---|---|
| 4,711,245 A | | 12/1987 | Higgins et al. |
| 5,282,950 A | * | 2/1994 | Dietze et al. ............... 204/406 |
| 5,286,362 A | | 2/1994 | Hoenes et al. |
| 5,437,999 A | | 8/1995 | Diebold et al. |
| 5,438,271 A | * | 8/1995 | White et al. ................ 324/444 |
| 5,502,396 A | * | 3/1996 | Desarzens et al. ...... 204/403.02 |

(Continued)

FOREIGN PATENT DOCUMENTS

EP 1 304 566 A1 4/2003

(Continued)

OTHER PUBLICATIONS

Morris N. A., Cardosi M. F., Birch B. J., Turner A. P. F., An electrochemical capillary fill device for the analysis of glucose incorporating glucose oxidase and ruthenium (III) hexamine as mediator, 1992, Electroanalysis, 4, 1-9.*

*Primary Examiner*—Kaj K Olsen
*Assistant Examiner*—Bach T Dinh
(74) *Attorney, Agent, or Firm*—Larson & Anderson, LLC

(57) ABSTRACT

A substantially planar electrochemical test strip for determination of the presence and/or quantity of an analyte in a sample is provided that has a first electrode, a first connector including two contact pads, and a first conductive lead extending between the first electrode and the first connector to establish a path for conduction of an electrical signal between the first electrode and the first connector; a second electrode, a second connector including one or more contact pads, and a second conductive lead extending between the second electrode and the second connector to establish a path for conduction of an electrical signal between the second electrode and the second connector, and a sample chamber for receiving a sample. The first and second electrode are disposed to contact a sample within the sample chamber such that an electrochemical signal is generated. The contact pad or pads of the second connector are between the contact pads of the first connector when viewed in the plane of the test strip. A meter having contacts for use with the electrochemical test strip, and a combination of a meter and an electrochemical test strip are also provided.

23 Claims, 18 Drawing Sheets

U.S. PATENT DOCUMENTS

| | | | |
|---|---|---|---|
| 5,520,787 A * | 5/1996 | Hanagan et al. | 204/403.14 |
| 5,985,116 A * | 11/1999 | Ikeda et al. | 204/403.04 |
| 6,071,391 A * | 6/2000 | Gotoh et al. | 204/403.05 |
| 6,349,230 B1 * | 2/2002 | Kawanaka | 600/347 |
| 6,503,381 B1 | 1/2003 | Gotoh et al. | |
| 6,969,450 B2 * | 11/2005 | Taniike et al. | 204/403.01 |
| 2003/0042150 A1 | 3/2003 | Ryu et al. | |
| 2003/0150724 A1 * | 8/2003 | Kawanaka et al. | 204/403.02 |
| 2003/0201176 A1 | 10/2003 | Mills et al. | |
| 2005/0069892 A1 | 3/2005 | Iyengar et al. | |
| 2006/0037859 A1 | 2/2006 | Hodges et al. | |
| 2007/0017824 A1 | 1/2007 | Rippeth et al. | |

FOREIGN PATENT DOCUMENTS

| | | |
|---|---|---|
| EP | 1 382 968 A1 | 1/2004 |
| WO | WO 01/33216 A1 | 5/2001 |
| WO | WO 2005/022143 | 3/2005 |

* cited by examiner

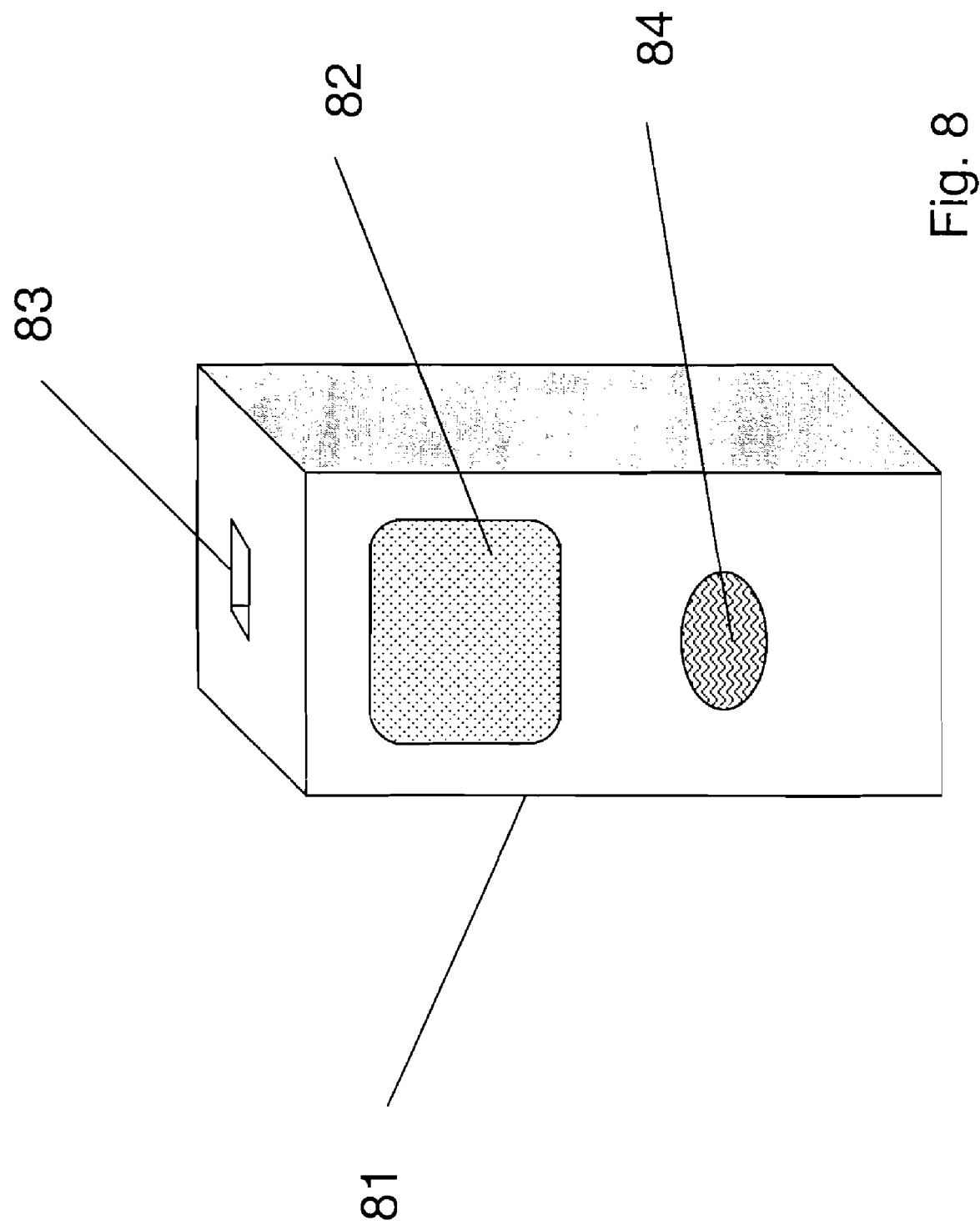

CONNECTOR CONFIGURATION FOR ELECTROCHEMICAL CELLS AND METERS FOR USE IN COMBINATION THEREWITH

This application claims the benefit of U.S. Provisional Application Ser. No. 60/521,555, filed May 21, 2004, which is incorporated herein by reference.

BACKGROUND OF THE INVENTION

This application relates to electrochemical cells, and particularly the type of cells configured as single-use strips that are used in home testing for analytes such as glucose.

Combinations of test strips and meters for the electrochemical detection of analytes such as glucose are known. In the test strip, there are routinely at least two electrodes between which an electrochemical signal is generated. The magnitude of this signal is indicative of the amount of the analyte present in the sample. The signal may be a measurement of current, that is an amperometric signal; a measurement of potential, that is a potentiometric signal, or a measurement of charge, that is a coulometric signal.

The electrodes which make actual contact with the sample to be evaluated for the presence and/or amount of analyte are connected to conductive leads, which in turn are connected to connectors, through which the strip is connected to a meter apparatus for detection and processing of the electrochemical signal to provide an indication of presence and/or amount of analyte to the user. The use of a separate meter allows the use of disposable electrode strips, and reusable electronics.

In general, in known disposable electrode strips, the strip is a flat rectangular strip with a top and a bottom major surface, two long sides, and two short sides or ends. Sample is generally introduced at one end, and the connectors are generally disposed at the opposite end. One lead/connector combination is provided for each electrode, and the leads and the associated connectors are generally disposed in a side-by side orientation parallel to the long sides of the strip.

This configuration of the connectors represents the accepted standards. It has one significant drawback, however, in that insertion of the strip into the meter is only correct in one direction. If the connectors are only on one surface of the strip (for example, the top), the insertion of the strip upside down (that is with the top surface down) may result in no electrical connection. It would be desirable to have an electrode connector configuration that overcomes this drawback.

SUMMARY OF THE INVENTION

The present invention provides a substantially planar electrochemical test strip for determination of the presence and/or quantity of an analyte in a sample, comprising:

(a) a first electrode, a first connector comprising two contact pads, and a first conductive lead extending between the first electrode and the first connector to establish a path for conduction of an electrical signal between the first electrode and the first connector, (b) a second electrode, a second connector comprising one or more contact pads, and a second conductive lead extending between the second electrode and the second connector to establish a path for conduction of an electrical signal between the second electrode and the second connector, and (c) a sample chamber for receiving a sample, said first and second electrode being disposed to contact a sample within the sample chamber whereby an electrochemical signal is generated, wherein the contact pad or pads of the second connector are between the contact pads of the first connector when viewed in the plane of the test strip.

The present invention further provides a meter having contacts for use with the electrochemical test strip, and a combination of a meter and an electrochemical test strip.

BRIEF DESCRIPTION OF THE DRAWINGS

FIG. 8 shows an exterior view of a meter in accordance with the invention.

DETAILED DESCRIPTION OF THE INVENTION

Figure 1A:
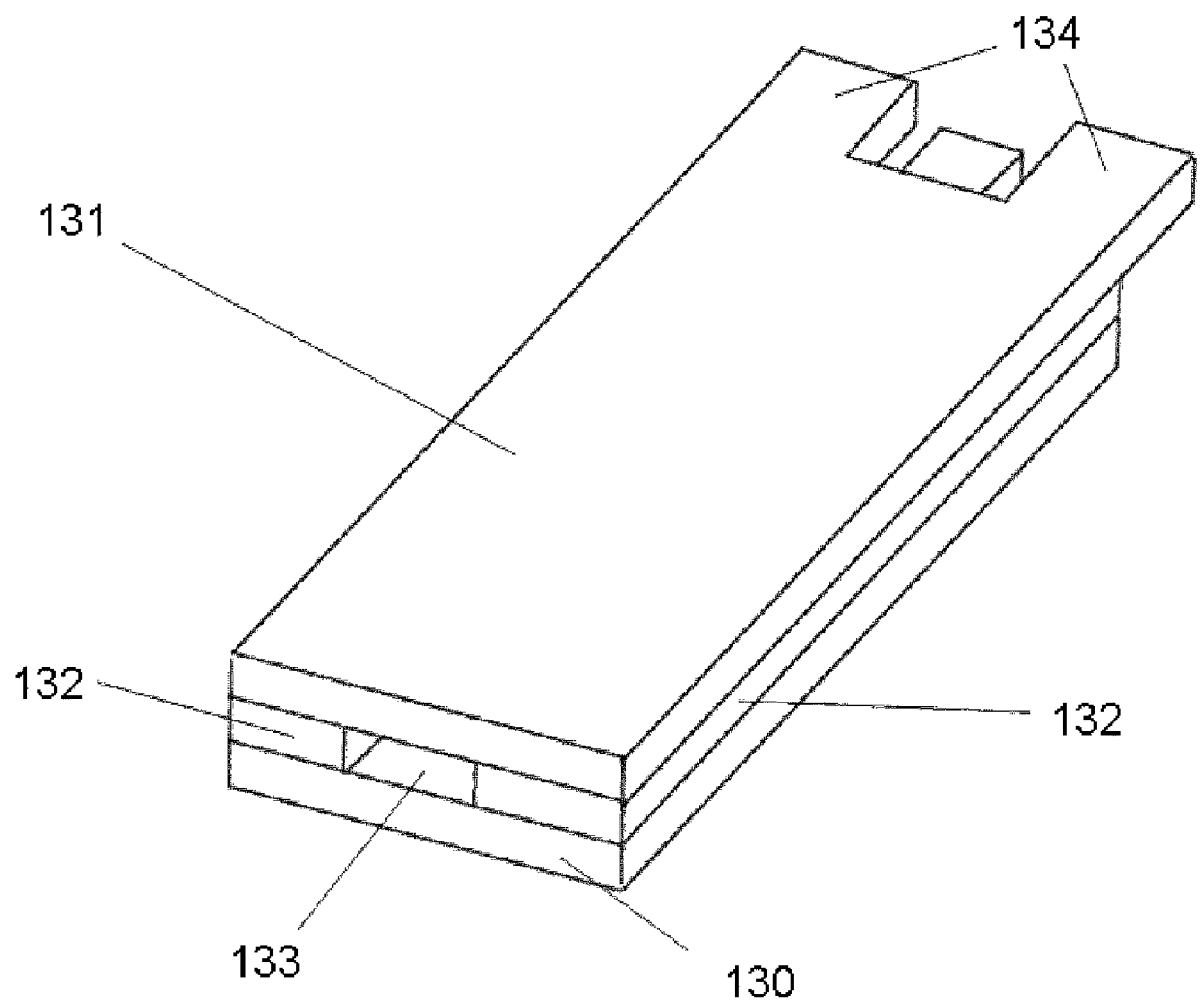
FIGS. 1A and B shows an isometric view of an electrochemical cell produced by the method of this invention.

The present invention provides electrochemical test strips that have a configuration for the connectors that provide substantial advantages over known connector configurations. The invention also provides meters that are adapted for receiving such electrochemical test strips, and combinations of meters and test strips. Although primarily illustrated in this application in the context of measurement of glucose levels in blood or other fluids, the connector configuration of the invention is suitably employed in electrochemical test strips for other electrochemically detectable analytes.

As used herein, the term "analyte" refers to substance for which a test is performed. The test may be qualitative (a measurable signal associated with the analyte is or is not detectable), semi-quantititave (a measurable signal above or below a specified threshold provides a positive or negative indication) or quantitative (a numerical value of the amount of analyte is provided).

As used herein the phrase "determination of an analyte" encompasses determination of the presence or amount of an analyte in any of these types of tests.

As used herein, the term "sample" refers to any type of sample in which the determination of an analyte is desirable. This would include without limitation bodily fluids, for example blood, urine, sputum, interstitial fluid, or saliva; commercial products, but other samples including beverages such as wine or soda, waste water, and other liquids may also be tested using the invention. Samples that are not liquids may be suspended or dissolved in an aqueous solvent.

As used herein, the term "electrode" refers to a conductive element which in use is in contact with the sample. Two or more electrodes in contact with the same sample for an electrochemical cell. In a two electrode system, the electrodes are conventionally referred to as a working and counter electrode. In a three electrode system, the third electrode is conventionally referred to as a reference electrode. The electrode material employed is selected consistent with the nature of the analyte and the electrochemical reactions to be monitored, and suitable electrode materials for specific analytes are known in the art. Non-limiting examples of electrode materials include gold, silver, PT, Ag/AgCl and conductive carbon. The electrodes in a given electrochemical strip may be formed from the same material or from different materials, The term "connector" refers to a portion of an electrochemical strip that is designed for contact with a meter that provides any necessary electrochemical impetus to the electrochemical strip and receives input from the strip for analysis and display to the user. The connectors may be made from the same material as the electrode to which they are connected, or of different materials.

Each connector is in electrical contact with the electrode via a conductive "lead." A lead may be made of the same material as the electrode, the same material as the connector, the same material as both the electrode and the connector or different materials from both the electrode and the connector between which the lead extends.

As used herein, the term "contact pad" refers to the portion of the connector that is actually contacted with a corresponding contact in the meter when in use. As reflected below, a connector may have a single contact pad, in which case the contact pad may be only the terminal portion of the connector, or may be coextensive with the connector. In cases where the connector comprises a plurality of contact pads, the contact pad are electrically isolated one from the other except for conductive paths leading through the remainder of the connector, the lead, or the electrode with which they are associated.

In the present invention, the contact pad or pads of the second connector are between the contact pads of the first connector when viewed in the plane of the test strip. This does not require that the pads are exactly coplanar, and indeed in the examples shown herein the contact pads are not coplanar. They are, however, disposed in the stated orientation when the test strip is viewed in a plan view looking towards a major surface of the electrochemical test strip.

FIG. 1A shows schematic representation of an embodiment of an electrochemical test cell of the invention, viewed from the sample application end. The cell is formed from a bottom layer 130, a top layer 131, and a middle layer 132. The top and bottom layers are electrically conductive, at least on the surfaces facing the middle layer 132. In preferred embodiments, the top and bottom layers 130, 131 are an insulating substrate onto which a conductive layer has been coated. As more clearly shown in FIG. 1B in which the top layer 131 has been removed, the middle layer 132 has a notch 133 formed in one edge. The notch 133, and the top and bottom layers 130, 131 together define a space into which sample is received when the electrochemical cell is in use. The volume of this space is thus defined by the thickness of the middle layer 132 and the dimensions of the notch. The electrochemical cell also has connectors having contact pads thereon 134 and 135 that are attachable to a meter to provide an electrical connection between the meter and the portion of the top and bottom layers 130, 131 that are exposed in the space for receiving a sample.

The middle layer 132 is an electrically resistive material which isolates the conductive layers, and prevents electrical conductivity between the electrically conductive top and bottom layers 130, 131, unless they are connected via a sample disposed in the space for receiving a sample. Non-limiting examples of suitable materials for use as this layer include polyimide, polyester, polyethylene terephthalate (PET), polycarbonate, glass, fiberglass or other nonconductive materials that provide the desired support. The middle layer 132 suitably has a thickness of 500 to 50 micrometers. Thicker materials can be used where larger sample volumes are acceptable. Thinner materials can be used, but may create difficulties in handling, and increased difficulty in drawing sample into the finished cell since this thickness determines one dimension of the sample space. In a preferred embodiment of the present invention, the sample space volume is less than 5 microliters and more preferably less than 1 microliter. In specific embodiments of the invention, the volume of the sample space is 500, 300, 200, 100 or 50 nl.

The conductive portion of top and bottom layers 130, 131 is selected consistent with the specific analyte that the electrochemical cell is intended to detect. Specific examples of suitable conductive electrode materials include gold, carbon, silver, palladium, and platinum. The conductive material used in the top and bottom layers 130, 131 may be the same or they may be different from one another. In a preferred embodiment of the present invention the conductive material is gold. The conductive portion of the top and bottom layers is suitably a thin coating on one surface of an insulating substrate sheet. Materials used for the middle layer 132 may be used as this substrate as well.

Depending on the analyte to be detected, the electrochemical cell may include a reagent composition disposed within the space for receiving a sample. In the case of an electrochemical cell for the detection of glucose, this reagent composition suitably comprises an enzyme effective to oxidize glucose, for example glucose oxidase, and a redox mediator, for example ferricyanide. Reagent compositions for this purpose are known in the art, for example from U.S. Pat. No. 4,711,245 to Higgins et al. and U.S. Pat. No. 5,437,999 to Diebold et al., which are incorporated herein by reference. In a particular embodiment of the reagent comprises glucose oxidase and ferricyanide.

In addition to its electrochemical function, the reagent composition, when present, may assist in overcoming the hydrophobicity of the sample space, so that blood or other aqueous sample can be drawn into the space by capillary action. Where a reagent is not used, surface treatment of the sample volume to reduce hydrophobicity and to facilitate sample introduction may be indicated.

As shown in FIGS. 1A and B, the test strip of the invention is substantially planar. This means that the test strip has a top substantially planar surface and a bottom substantially planar surface that are substantially parallel. The term "substantially" is included in this statement to encompass deviations from perfect planarity and parallelness that result from manufacturing variations in the thickness of materials used across the length and width of the strip, variations in the thickness of depositions such as film, ink or adhesive depositions across the length and width of the device and the like.

Figure 1B:
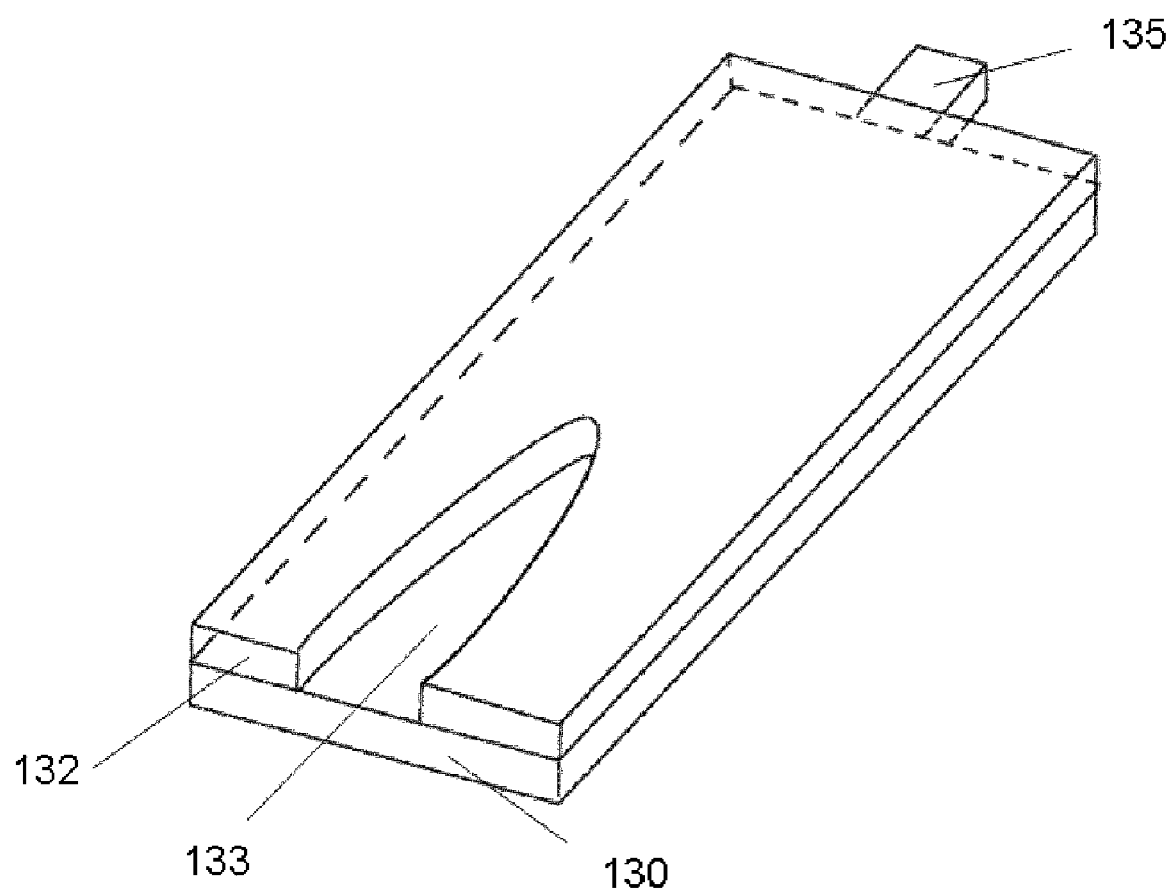
Figure 2A:
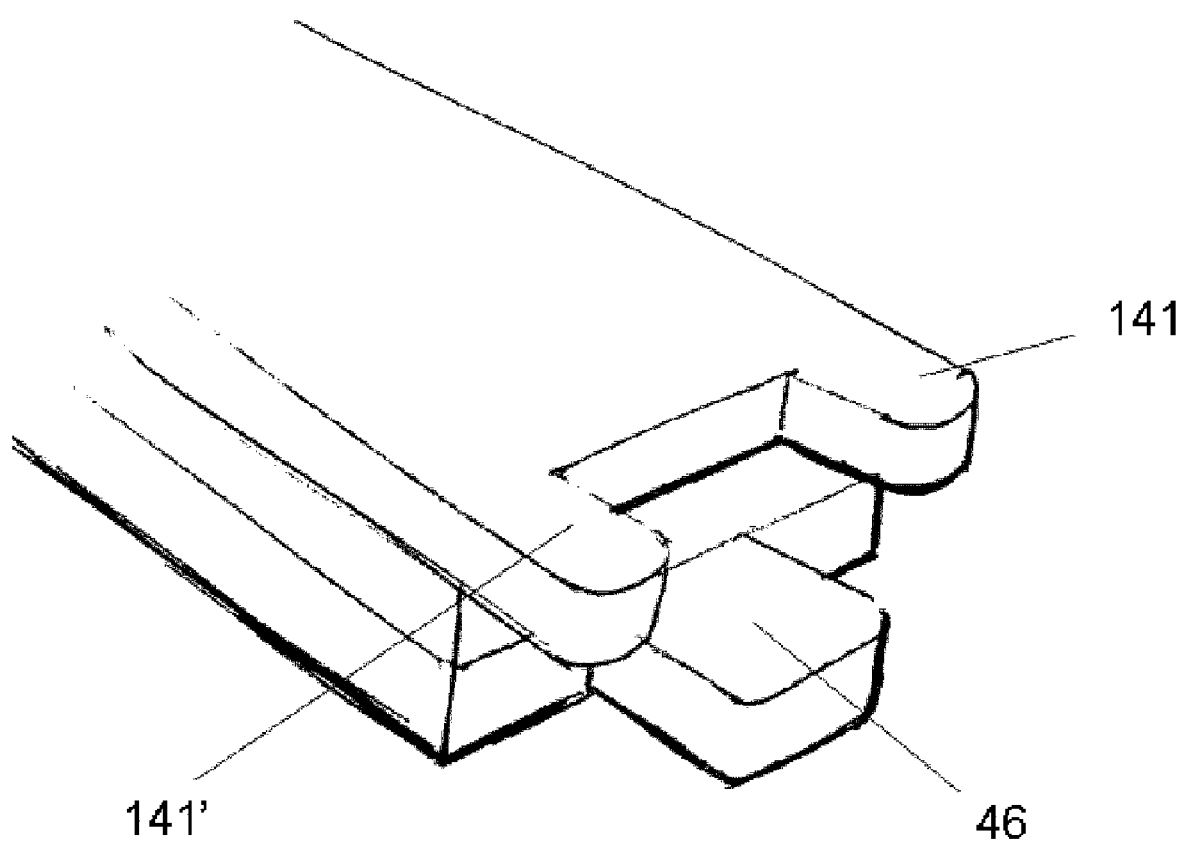
FIGS. 2-A and B show embodiments of connector configurations of electrochemical test cells of the invention.
Figure 2B:
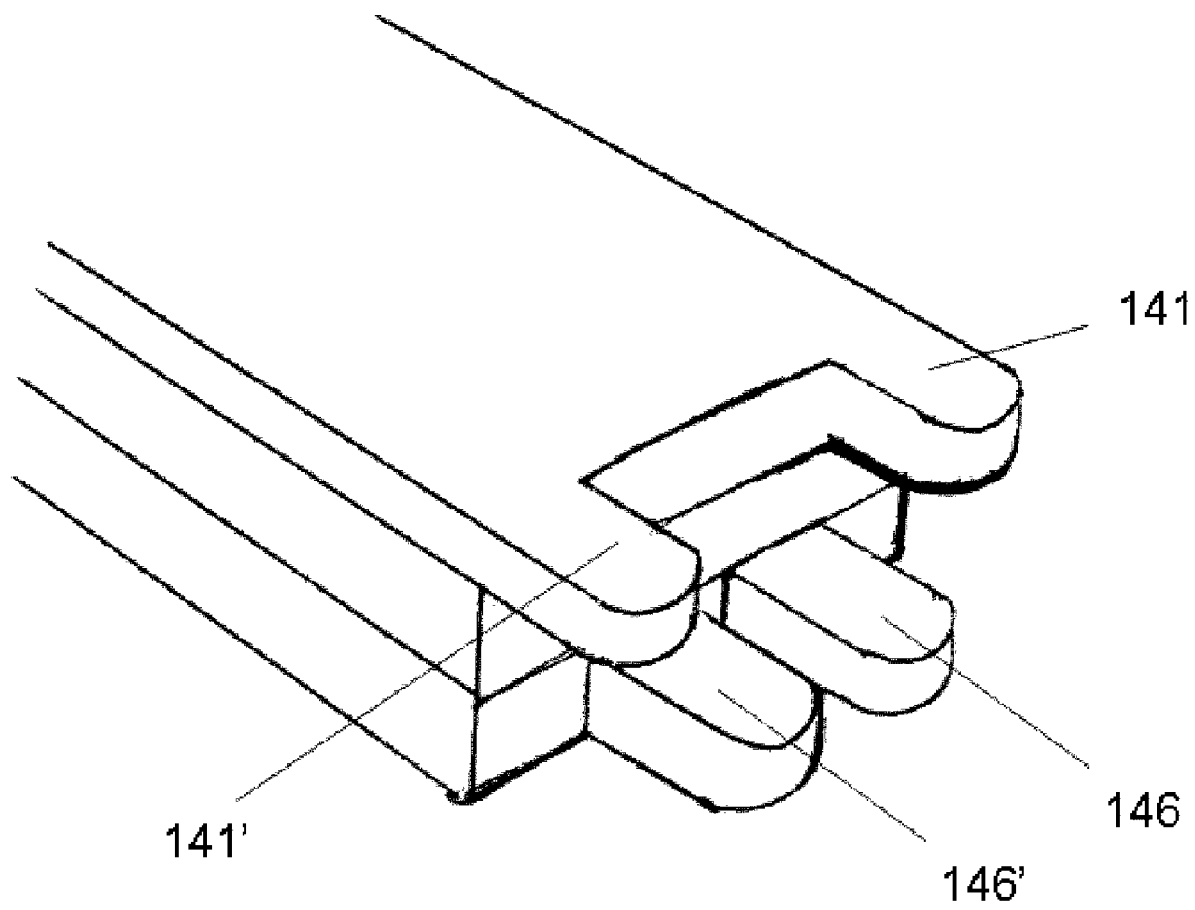

The present application relates to the design of the connectors in test strips such as that shown in FIGS. 1A and 1B. FIGS. 2A and B show embodiments of connector configurations in accordance with the invention. In FIG. 2A, there are two peripherally located connectors having contact pads thereon, 141, 141' that extend from the top conductive layer and one centrally located connector having a contact pad thereon 46 extends from the bottom conductive layer. FIG. 2B shows an alternative embodiment in which two peripherally located connectors having contact pads thereon, 141, 141' extend from the top conductive layer and two centrally located connectors having contact pads thereon 146, 146' extend from the bottom conductive layer.

The connector/contact pad configurations shown in FIGS. 2A and B provide an important advantage in the use of disposable electrochemical test strips. Because the contact pads for the first electrode are always disposed at the periphery of the test strip, and the contact pads for the second electrode are always disposed centrally, meters can be designed which accept the strip in either of two orientations without ambiguity as to the electrode that is associated with the contacts of the meter. Such meters are discussed in greater detail below.

Figure 3:
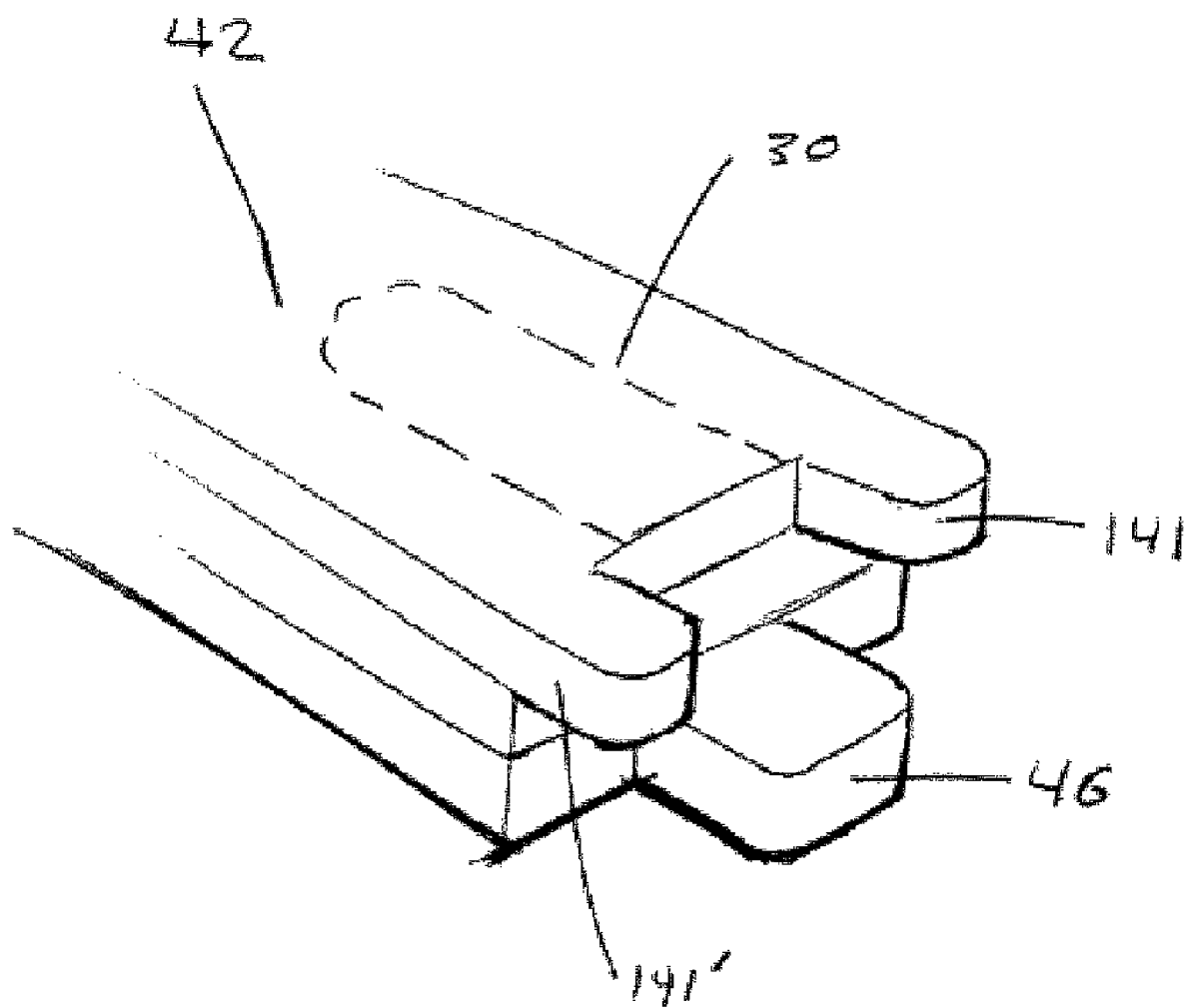
FIG. 3 shows an electrochemical test cell of the invention.

FIG. 3 shows a further embodiment of the electrochemical test strip of the invention. FIG. 3 is generally similar to FIG. 2A, except that the division of the connectors having contact pads thereon 141, 141' is continued through some or all of the balance of the connector (if any) and the lead as reflected by dashed line 30 which reflects a scoring or removal of the conductive surface on the underside of layer 42.

Figure 4:
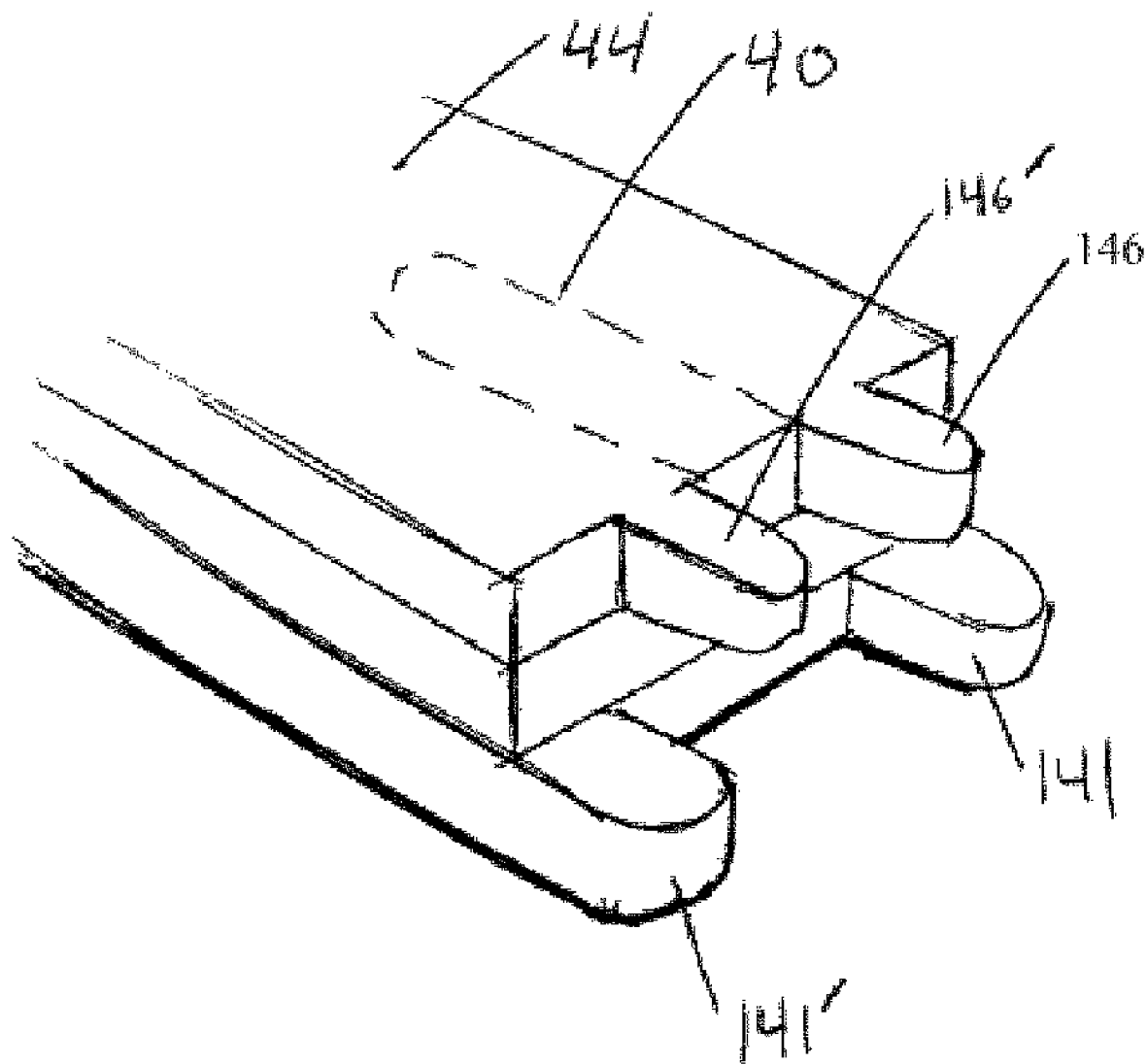
FIG. 4 shows an electrochemical test cell of the invention.

FIG. 4 shows a further embodiment of the electrochemical test strip of the invention. FIG. 4 is generally similar to FIG. 2B (shown from the bottom), except that the separation of the connectors having contact pads thereon 146, 146' is continued through some or all of the balance of the connector (if any) and the lead as reflected by dashed line 40 which reflects a scoring or removal of the conductive surface on the underside of layer 44.

The separation of connectors and leads as shown in FIGS. 3 and 4 can be used in combination in a single device.

Figure 5:
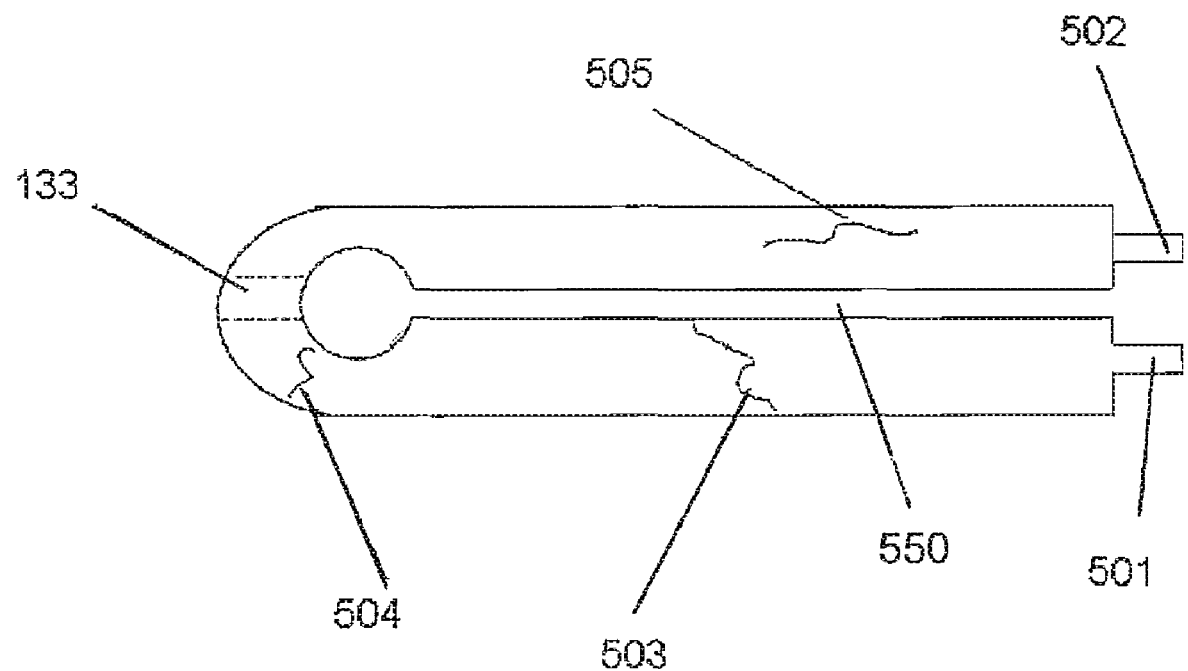
FIG. 5 shows one electrode layer of an electrochemical test cell of the invention.

The connector configurations shown in FIGS. 3 and 4 provide advantages in the area of fault testing prior to the application of a sample when there is (or should be) no electrical contact between the electrodes. Damage to one of the electrodes or its associated leads that extends completely across the path of electrical connection will prevent the completion of the circuit necessary for measurement. However such damage is not detectable in a conventional electrochemical strip prior to application of the sample, the electrode and its associated leads are not part of a circuit that can be measured. As shown in FIG. 5, however, when the separation of the contact pads on connectors 141, 141' (or 146, 146') is extended, the two contact pads can be used as ends of a circuit to confirm the continuity of the area around the sample cell.

FIG. 5 shows just the electrode layer of a cell where the connectors having contact pads thereon 501 and 502 have an extended separation 550. The location of the sample space 133 is shown in dashed lines. If the electrical connection (for example via a conductivity measurement) is assessed between connectors having contact pads thereon 501 and 502, a good connection will be determined provided that there is no damage to the conductive sheet that extends all the way across either leg or the loop portion of electrode layer. For example, a scratch 503 or 504 would be detected as a fail, while a scratch such as 505 would not. Since connection between the electrode portion over the sample space 133 and either one of the connectors having contact pads thereon 501 or 502 is sufficient for a valid test result, this provides an easily achieved, non-destructive form of quality control which is actually more rigorous than the requirements of the operative device.

The ability to test the strip for electrical continuity before application of a sample presents a decided advantage from the user perspective. In the case of many diabetics, tests are performed several times a day, each test requiring that the user prick himself to obtain the sample. Because of small sample size required, a failed test strip may require an additional prick with the lancet. Being able to test the strip to check for common manufacturing problems before the sample is collected reduces the risk of needing multiple pricks, or the risk that a user will opt out of a needed test to avoid a second prick.

Figure 6:
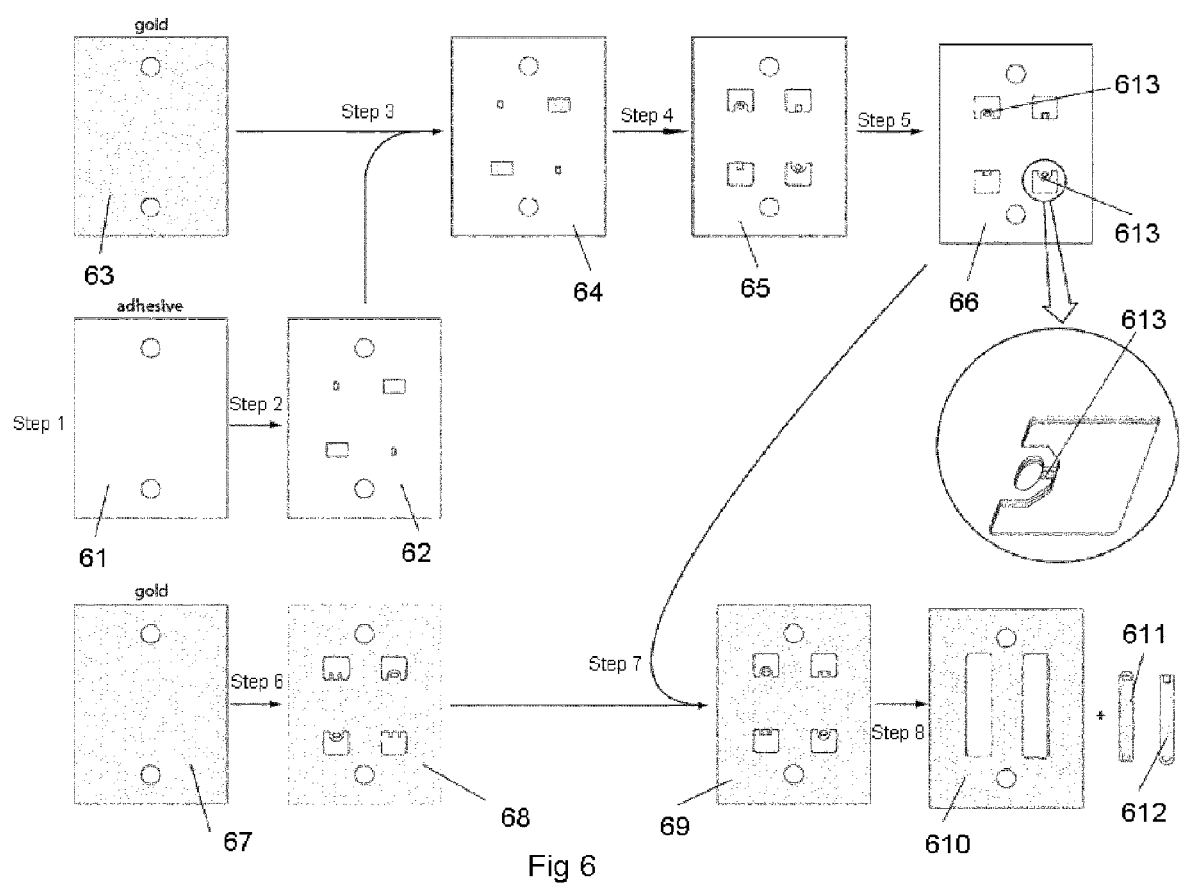
FIG. 6 shows a process for making electrochemical test cells of the invention.
Figure 7A:
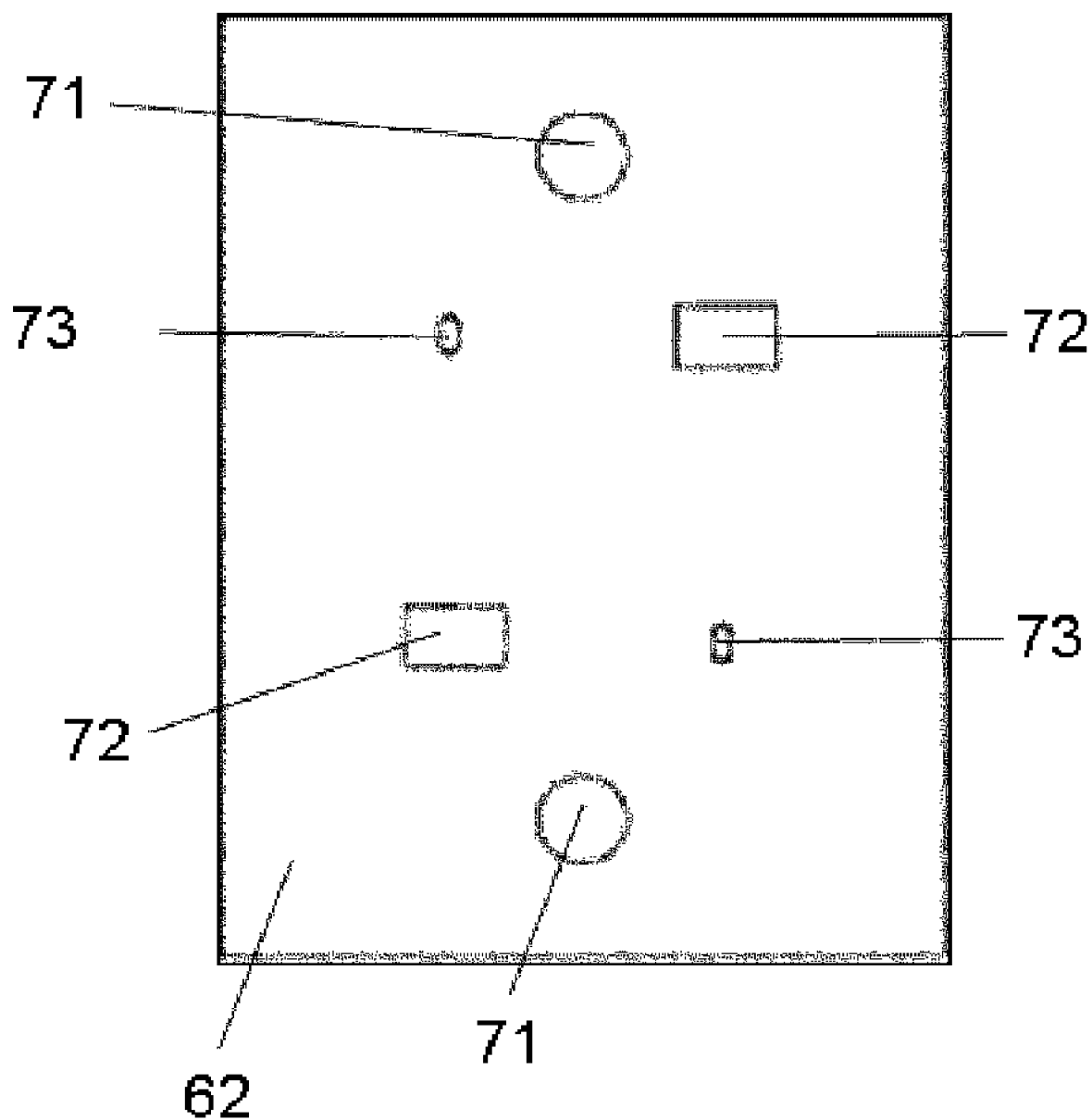
FIGS. 7A-C show intermediate stages in a method of manufacture of electrochemical test cells of the invention.
Figure 7B:
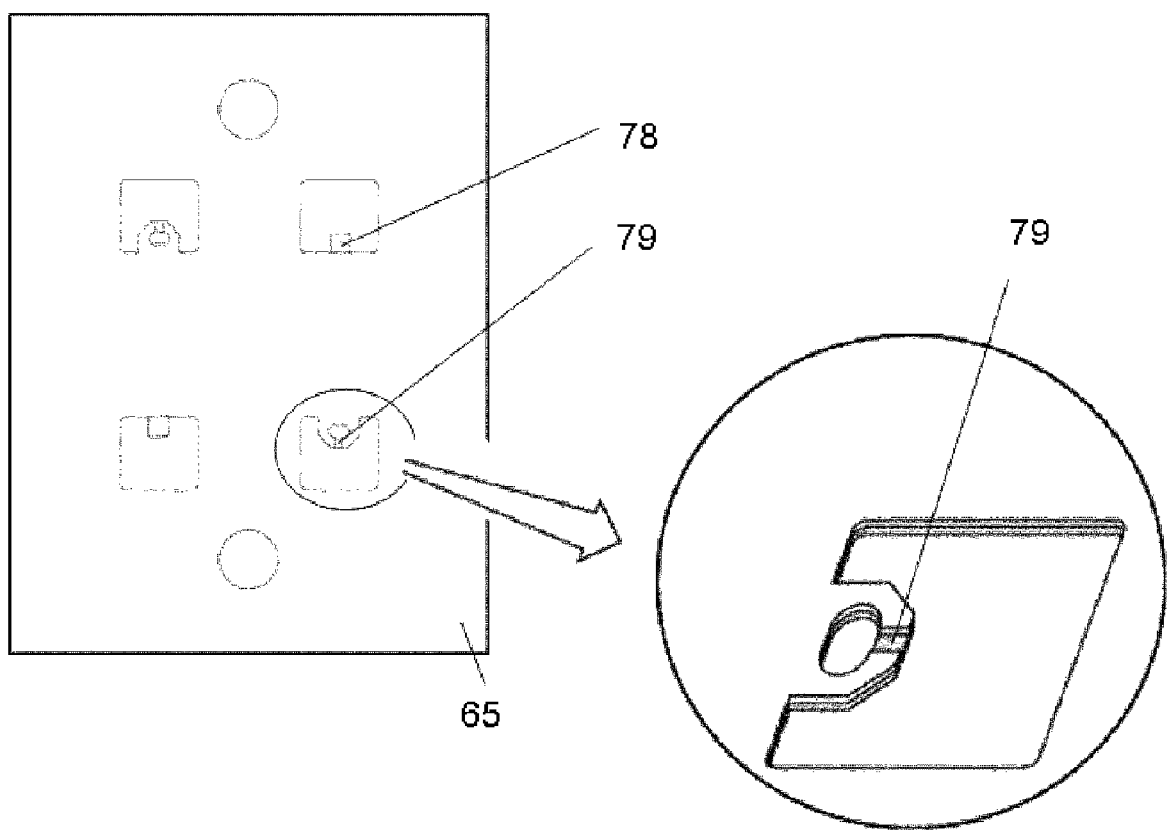

Electrochemical test strips in accordance with the invention can be manufactured using the method as illustrated in FIGS. 6, 7A and 7B and as described in U.S. patent application Ser. No. 10/909,656 filed May 20, 2005, which is incorporated by reference.

Step One: An electrically resistive sheet is provided. The electrically resistive sheet 61 is coated with an adhesive on both major surfaces thereof.

Step Two: As shown in detail in FIG. 7A, two registration holes 71 are provided to the electrically resistive sheet 61 from step one for manufacturing alignment and do not become part of the final device. The electrically resistive sheet 61 is placed into a die assembly (not shown) wherein the die assembly aligns the electrically-resistive sheet via the two registration holes. The electrically resistive sheet 61 is then punched thereby forming a punched electrically-resistive sheet 62 with two large and two small openings through the sheet. The large openings 72 are the openings through which the electrical connectors will be formed. The small openings 73 are the openings across which the notching opening, and the vent opening will be made define the sample space.

Step Three: The punched electrically resistive sheet 62 is then adhered to a first electrically conductive sheet 63 thereby forming a combined sheet 64. The electrically conductive sheet has at least one surface coated with a conductor, for example gold, which faces the punched electrically resistive sheet 62, and includes two registration holes in alignment with the registration holes of the electrically resistive sheet 62. Once the combined sheet 64 is formed, the conductive surface of the first electrically conductive sheet 63 is visible through the openings in the punched electrically resistive sheet 62.

Step Four: The combined sheet 64 is punched, thereby forming a punched combined sheet 65. FIG. 7B shows this punched combined sheet 65 in greater detail. The punched combined sheet 65 is cut such that both the proximal and distal ends of the rectangular opening are cut off, leaving the start of a generally rectangular/square sample space 79. The punch of step four also defines a first electrical connector 78 through which the electrode formed from the first electrically conductive sheet may be electrically connected with a measuring device.

Step Five: For purposes of making an electrochemical strip for requiring an external reagent, a reagent 613 is added to the punched combined sheet 65 over the sample space 79, thereby forming a reagent sheet 66. For a glucose sensor, the reagent that is added to the punched combined sheet 65 suitably comprises glucose oxidase and a redox mediator comprising ferricyanide. Preferably, the mediator is added in a liquid carrier that has a volume sufficient to fill at least 50%, and more preferably a greater portion of the sample space. This results in a coating of the mediator higher on the walls of the sample space, and therefore closer to the second electrode. This decreases the time for mediator to reach the second electrode during use, and thus improves the response time of the device. Electrochemical cells in which this feature is claimed are described in International Patent Application No. PCT/IB2005/051659 which is incorporated herein by reference.

Figure 7C:
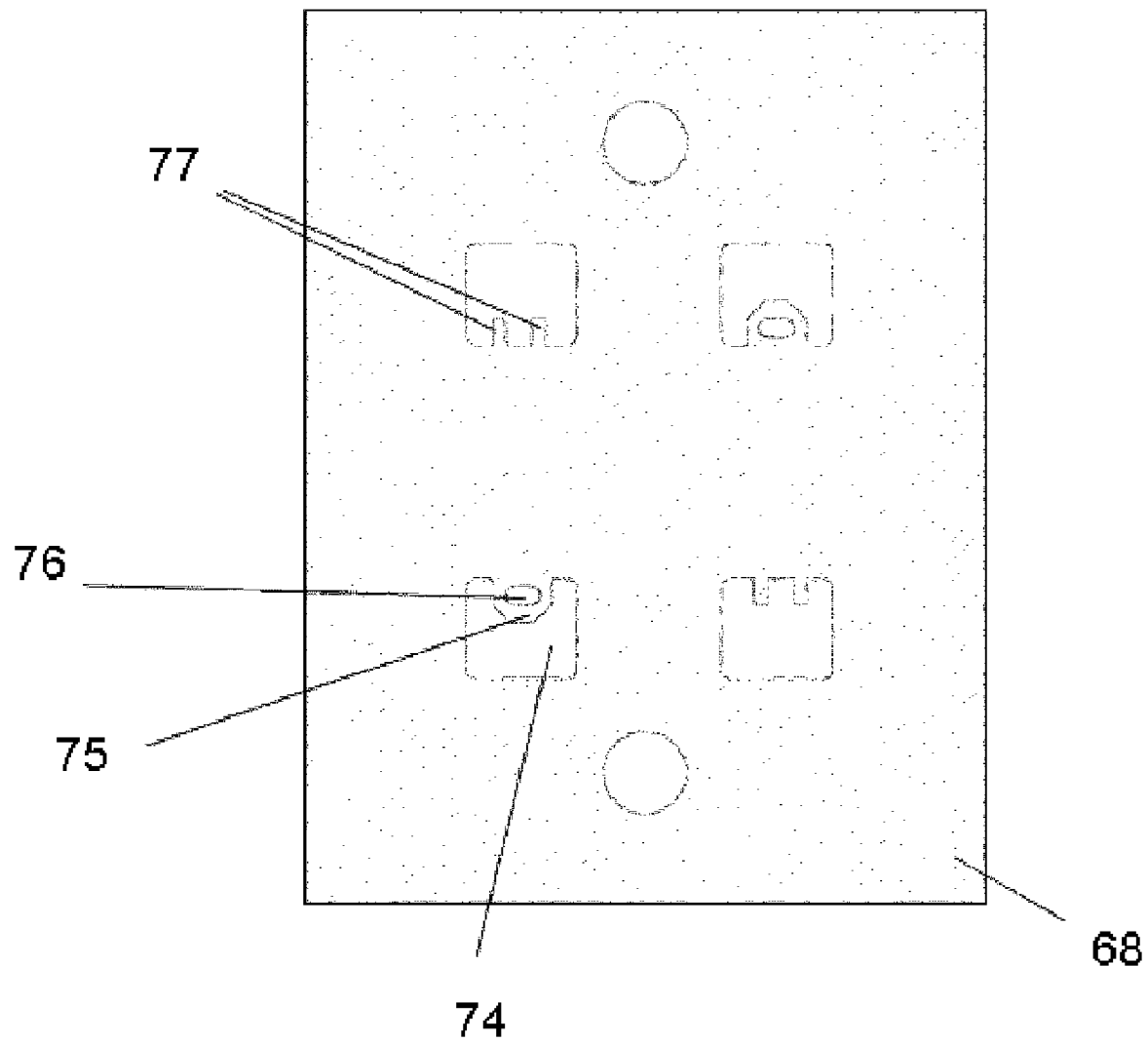

Step Six: Two registration holes are provided to a second sheet of an electrically conductive material 67. The two registration holes are for manufacturing alignment and do not become part of the final device. Electrically conductive sheet 67 is placed into a die assembly (not shown) and is punched thereby forming an opposite electrode sheet 68. The punch used defines the top electrode for the sample space. Thus, as shown in FIG. 7C, punched opening 74 defines a device tip 75 and a vent hole 76 having the same shape as those in the punched combined sheet 65. The punch also defines a second connector area 77, for connecting the electrode formed from the second sheet of electrically conductive material. The punch forming the second connector area 77 is not the same as the punch forming connector area 78, since what is desired is two nested sets of accessible contacts that do not make electrical contact one with another.

The second electrically conductive sheet 67 is suitably of the same material and construction of the first electrically conductive sheet 63, although it may be made of a different material, or include a label.

Step Seven: Opposite electrode sheet 68 is adhered to reagent sheet 66 from step five thereby forming an electrochemical sheet 69, wherein the registration holes of the opposite electrode sheet align with the registration holes of the reagent sheet. The conductive portion of opposite electrode sheet 68 is in contact with the electrically resistive sheet of the reagent sheet 66. This step results in the definition of the sample space, bounded by the two electrically conductive sheets on the top and bottom, and the electrically resistive sheet on the sides, and having openings at each end.

Step Eight: Electrochemical sheet 69 from step seven is cleaved thereby forming a spent electrochemical sheet 610 and two free electrochemical cells 611 and 612. It will be appreciated however that the steps of this embodiment may be altered to result in a process that produces more than or less than two electrochemical cells from a starting sheet.

When used, the electrochemical test strips of the invention are inserted into a meter that has a contact configuration that matches the contact pads of the test strip. A sample is introduced to the sample receiving space either before or after the test strip is placed in the meter. Depending on the nature of the electrochemical reaction and analysis, a current, a potential difference or a charge may be applied to the electrodes. Alternatively, spontaneous electrochemistry occurring at the surfaces of the electrodes may be monitored.

FIG. 8 shows an exterior view of an exemplary, non-limiting embodiment of a meter in accordance with the invention, The meter generally comprises a housing 81 with a slot 83 for receiving an electrochemical test strip, and means for communicating the result of the test to a user. In FIG. 8, the means for communicating the result is a visible display, for example an LCD display 82, which provides the user with a numerical value for the amount of analyte. Other means for communicating the result include a binary semi-quantitative display, for example in the form of an LCD or LED display, a wireless data transmission system, for example a 102.11 b or 102.11 g wireless data transmission link, an infrared data transmission link or a cell phone link, or a connector to which a cable can be attached, or example a USB cable, a RS-232 serial cable or a parallel cable. The meter may also include an on switch to start the measurement cycle if desired or buttons such as button 84 to control meter operation and display. These elements can be used in various combinations and are reflected in numerous meters known in the art.

Figure 9A:
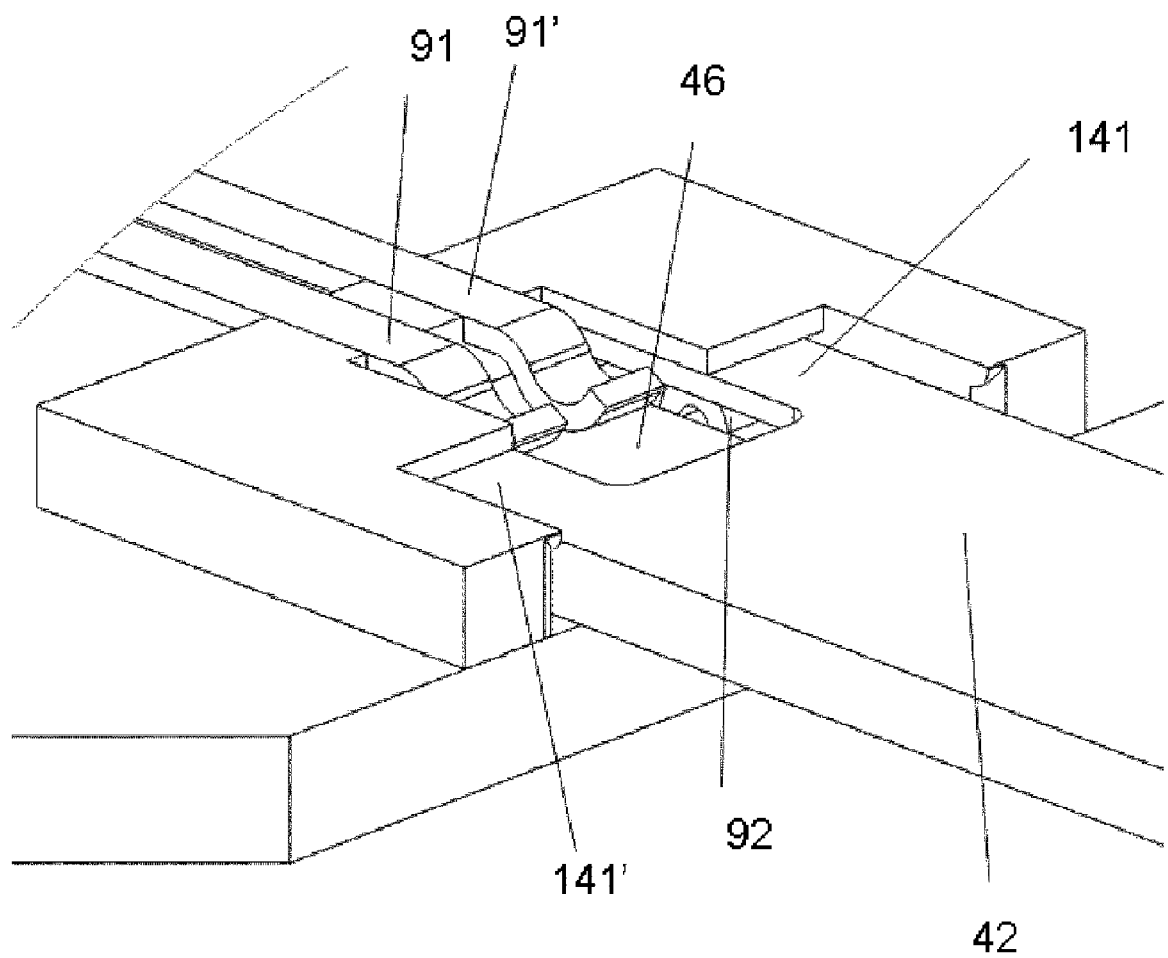
FIGS. 9A-C show the connection of a electrochemical test strip to a meter in accordance with an embodiment of the invention.
Figure 9B:
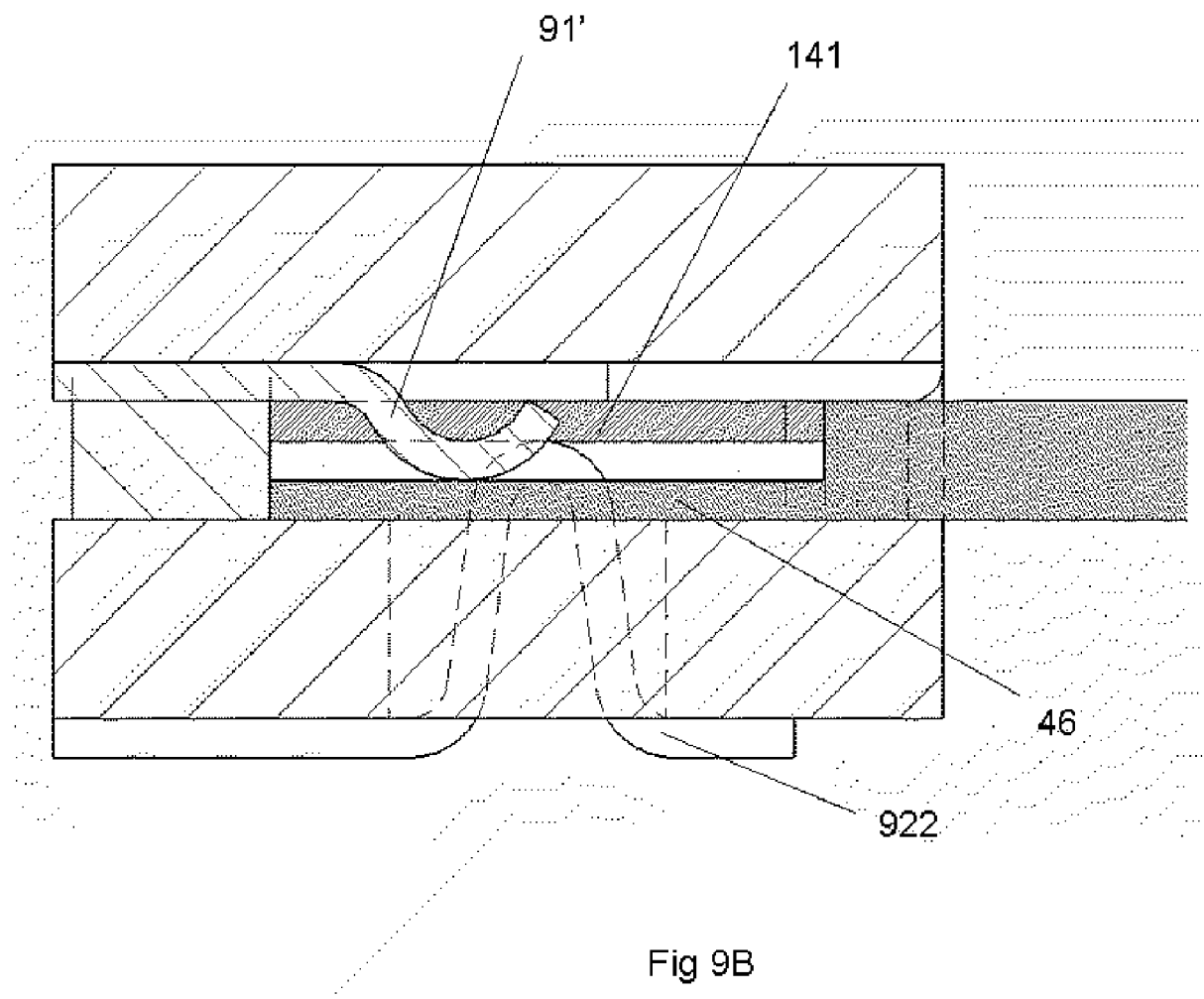
Figure 9C:
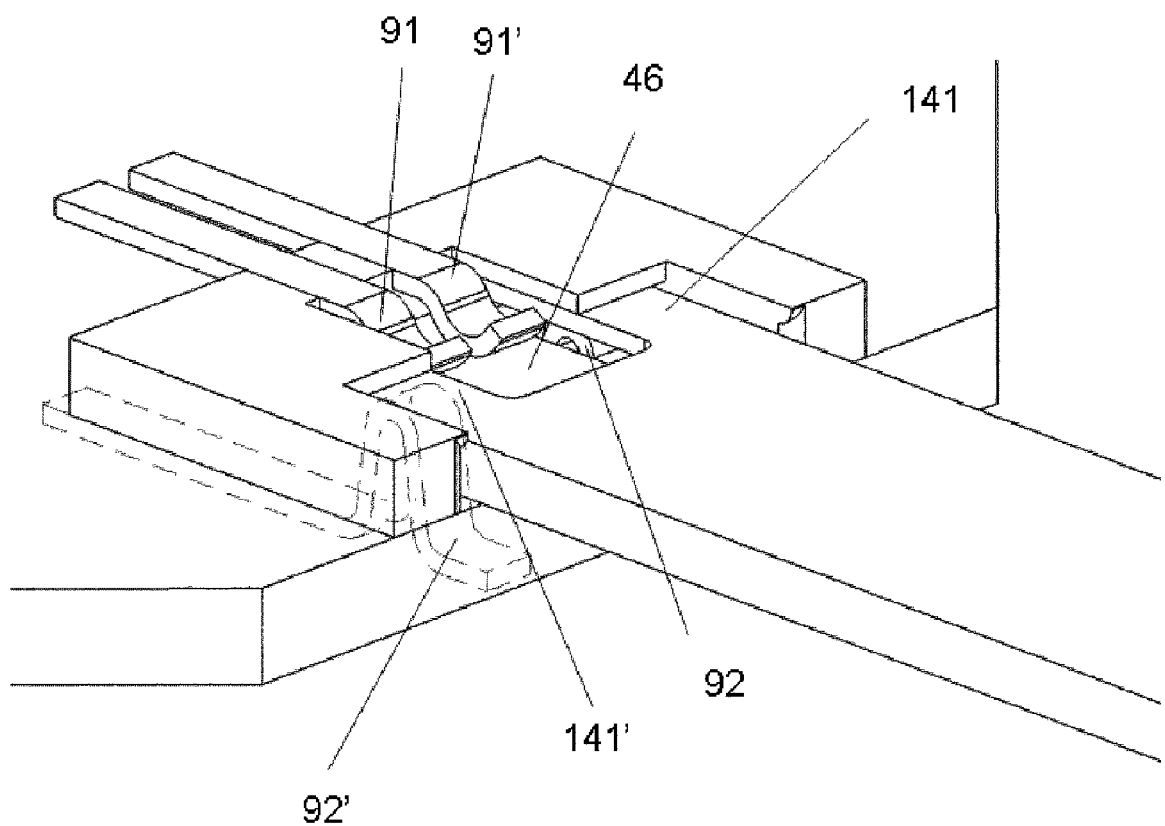

FIGS. 9A-C show the interior of the slot 83 in which meter contacts corresponding to the contact pads of FIG. 3 are shown. In FIG. 9A, meter contacts 91 and 91' bear on electrochemical test strip contact pad on connector 46 in the area between the connector tabs 141 and 141' (on which electrochemical test strip contact pads are disposed). Meter contacts 92 and 92' make contact with the bottoms of electrochemical test strip connector tabs 141 and 141' (on which surface the strip contact pads are disposed) and more clearly show in the views shown in FIGS. 9B and C.

Figure 10A:
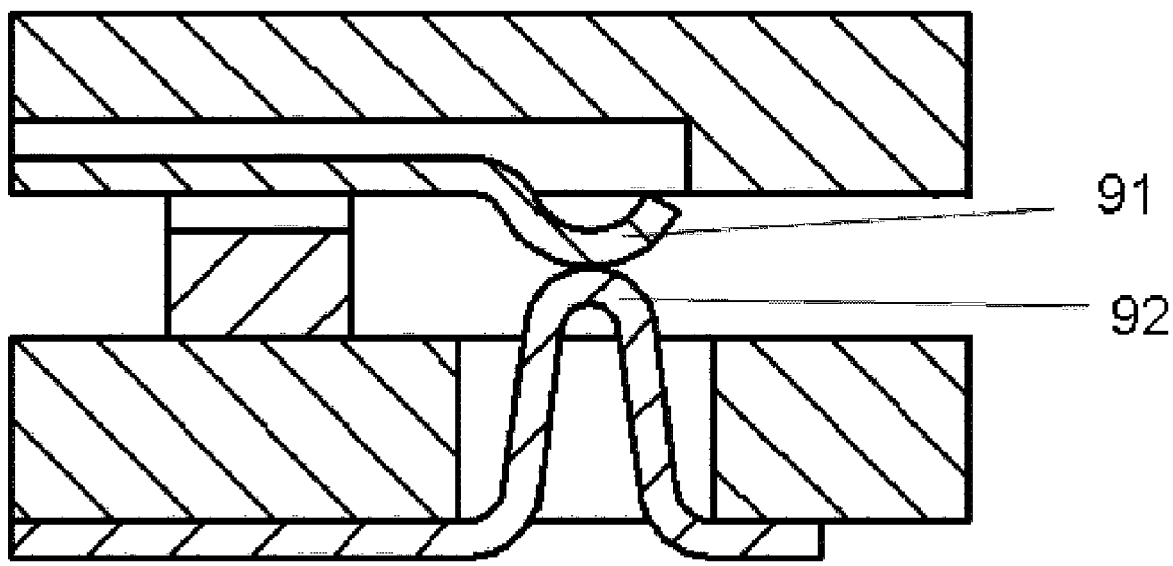
FIGS. 10A-C show the connection of a electrochemical test strip to a meter in accordance with another embodiment of the invention.
Figure 10B:
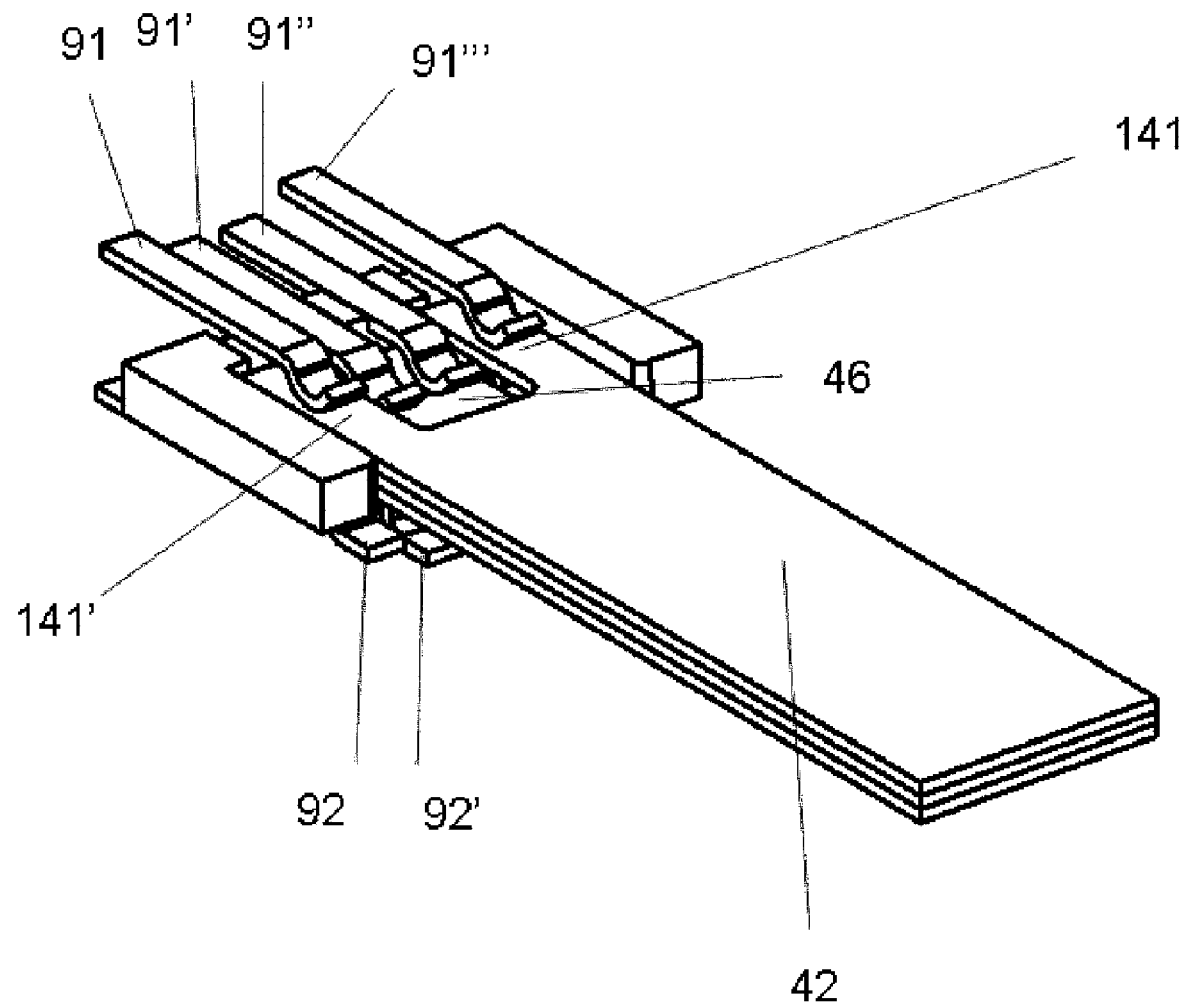
Figure 10C:
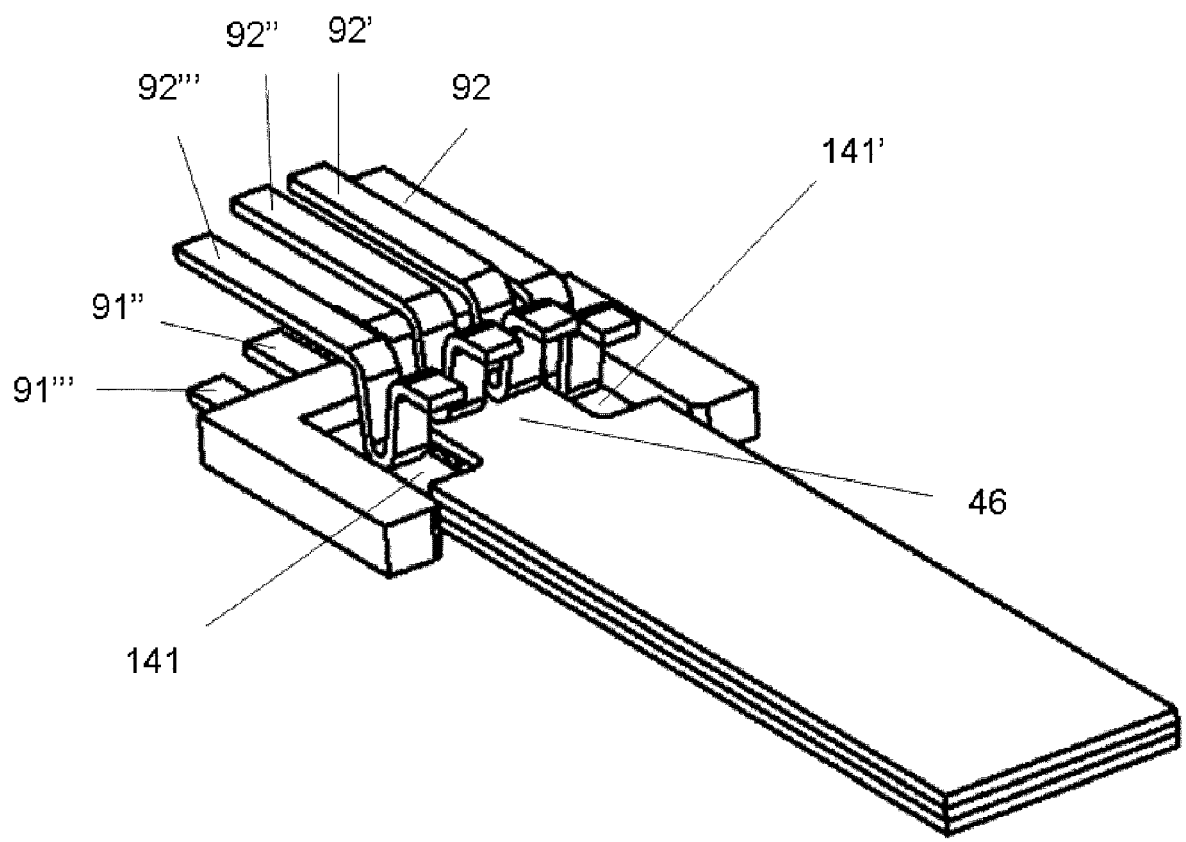

FIGS. 10A-C show another embodiment of the invention in which there are corresponding aligned connector pins that can make contact with the strip when it is inserted in either orientation, up or down. FIG. 10A shows a side-view where only meter contacts 91 and 92 are visible. In this illustration, each of the meter contact pins are in contact with their facing meter contact pin when a strip is not inserted; however, this is not a requirement. The meter contacts should allow for a strip to be inserted, either by being spaced apart by an appropriate gap or by allowing for deflection and/or bending upon insertion of a strip, either of which is referred to herein as a "space" between the contacts. FIG. 10B shows a top view of the meter contacts when a strip is inserted and illustrates meter contacts 91, 91', 91", and 91'''. FIG. 10C shows a bottom view of the meter contacts when a strip is inserted and illustrates meter contacts 92, 92', 92", and 92'''. Since each of these meter contacts can be addressed separately by the meter, it is possible for the meter to apply testing current or voltage to confirm the electrical continuity of the strip assuming the strip has an extended separation in the lead portion of the connector. Thus, in the example of FIGS. 10B and 10C, the meter would measure low resistance between meter contacts 91' and 91" and between meter contacts 92''' and 92 when there is electrical continuity in the strip.

The invention also provides a method for evaluating the electrical continuity of an electrochemical test strip for determination of an analyte in a sample prior to the application of that sample, comprising the steps of:

(a) inserting the test strip into a meter, wherein the test strip comprises:

a first electrode, a first connector comprising two contact pads, and a first conductive lead extending between the first electrode and the first connector to establish a path for conduction of an electrical signal between the first electrode and the first connector, a second electrode, a second connector comprising one or more contact pads, and a second conductive lead extending between the second electrode and the second connector to establish a path for conduction of an electrical signal between the second electrode and the second connector, and a sample chamber for receiving a sample, said first and second electrode being disposed to contact a sample within the sample chamber whereby an electrochemical signal is generated, and wherein the contact pads of the first connector are separated by a separation, and this separation is extended through a portion of the lead of the first connector.

(b) observing current flow or resistance between the contact pads of the first connector in a pathway through the first electrode, wherein low current flow or high resistance relative to an acceptable standard value is indicative of poor electrical continuity.

Within the meter of the invention are electronics that process the raw signal from the electrochemical test strip and convey it to the means for communicating the result. Specific approaches and apparatus for processing of this raw signal are known in the art, for example from U.S. Patent Publication No. U.S. 2005/0069892 A1, PCT Publication WO 2005/022143 and U.S. patent application Ser. Nos. 10/907,790 and 10/907,803, which are incorporated herein by reference. The specific electronics and signal processing methodology are not critical to the invention.

A further aspect of the invention is a combination of a meter and a test strip in accordance with the invention.

What is claimed is:

1. An electrochemical test strip for determination of the presence and/or quantity of an analyte in a sample, comprising:

(a) a first electrode, a first connector comprising two contact pads that are not in direct electrical contact with one another, and a first conductive lead extending between the first electrode and the first connector to establish a path for conduction of an electrical signal between the first electrode and the first connector, (b) a second electrode, a second connector comprising one or more contact pads, and a second conductive lead extending between the second electrode and the second connector to establish a path for conduction of an electrical signal between the second electrode and the second connector, and (c) a sample chamber for receiving a sample, said first and second electrode being disposed to contact a sample within the sample chamber whereby an electrochemical signal is generated, wherein the test strip is a substantially planar electrochemical test strip, the first and second connectors extend from a common edge of the electrochemical test strip and have open space therebetween, and wherein the contact pad or pads of the second connector are between the contact pads of the first connector when viewed in the plane of the test strip.

2. The test strip of claim 1, wherein the test strip has a first major surface and an opposing second major surface, and wherein the contact pads of the first connector are exposed on the first major surface, and the contact pad or pads of the second connector are exposed on the second major surface.

3. The test strip of claim 2, wherein the second connector comprises two contact pads disposed side-by-side in the plane of the test strip, said two contacts pads not being in direct electrical contact with one another.

4. The test strip of claim 1, wherein the second connector comprises two contact pads disposed side-by-side in the plane of the test strip, said two contacts pads not being in direct electrical contact with one another.

5. The test strip of claim 1, wherein the test strip has a first major surface and an opposing second major surface, and wherein the contact pads of the first connector are exposed on the first major surface and on the second major surface, and the contact pad or pads of the second connector are exposed on the first major surface and the second major surface.

6. The test strip of claim 5, wherein the second connector comprises two contact pads disposed side-by-side in the plane of the test strip, said two contacts pads not being in direct electrical contact with one another.

7. The test strip according to claim 1, wherein the contact pads of the first connector are separated by a non-conductive separation, and this non-conductive separation is extended through a portion of the lead of the first connector.

8. The test strip according to claim 7, wherein the second connector has two contact pads separated by a non-conductive separation, and this non-conductive separation is extended through a portion of the lead connector.

9. The test strip according to claim 1, wherein the second connector has two contact pads separated by a non-conductive separation, and this non-conductive separation is extended through a portion of the lead connector.

10. The test strip of claim 1, further comprising a reagent for detection of an analyte disposed within the sample chamber.

11. The test strip of claim 10, wherein the reagent comprises an enzyme effective to oxidize glucose and a redox mediator.

12. A meter for receiving a substantially planar electrochemical test strip for determination of an analyte in a sample, comprising (a) a slot for receiving the test strip, wherein the slot contains meter contacts for making electrical connection with a received test strip to connect the test strip to electronics of the meter, said contacts including a first set of electrode contacts disposed to make contact with two first electrode connectors comprising contact pads extending from opposite sides of a test strip end received in the slot, and a set of second electrode contacts disposed to make contact with a second electrode connector comprising a contact pad or pads centrally extending from the test strip end between the first electrode connectors comprising contact pads;

(b) electronics for processing a raw signal received via the meter contacts from the electrochemical test strip to produce a result for the determination of the analyte; and (c) means for communicating the result to a user, wherein the slot contains a top set of first electrode contacts and a bottom set of first electrode contacts, said top set of first electrode contacts and said bottom set of first electrode contacts having a space therebetween for receiving a test strip whereby the first electrode contact pads are in electrical contact with the top or bottom set of first electrode contacts and a top set of second electrode contacts and a bottom set of second electrode contacts, said top set of second electrode contacts and said bottom set of second electrode contacts having a space therebetween for receiving a test strip whereby the second electrode contact pads are in electrical contact with the top or bottom set of first electrode contacts.

13. An analyte measuring system comprising (a) a meter for receiving a substantially planar electrochemical test strip for determination of an analyte in a sample, comprising a slot for receiving the test strip, wherein the slot contains meter contacts for making electrical connection with a received test strip to connect the test strip to electronics of the meter, said contacts including a first set of electrode contacts disposed to make contact with two first electrode contact pads disposed at opposite sides of a test strip end received in the slot, and a set of second electrode contacts disposed to make contact with a second electrode contact pad or pads centrally disposed between the first electrode contact pads;

electronics for processing a raw signal received via the meter contacts the from the electrochemical test strip to produce a result for the determination of the analyte; and means for communicating the result to a user, wherein the slot contains a top set of first electrode contacts and a bottom set of first electrode contacts, said top set of first electrode contacts and said bottom set of first electrode contacts having a space therebetween for receiving a test strip whereby the first electrode contact pads are in electrical contact with the top or bottom set of first electrode contacts and a top set of second electrode contacts and a bottom set of second electrode contacts, said top set of second electrode contacts and said bottom set of second electrode contacts having a space therebetween for receiving a test strip whereby the second electrode contact pads are in electrical contact with the top or bottom set of first electrode contacts, and (b) a substantially planar electrochemical test strip received within the slot, where in the test strip comprises:

a first electrode, a first connector comprising two contact pads, and a first conductive lead extending between the first electrode and the first connector to establish a path for conduction of an electrical signal between the first electrode and the first connector, a second electrode, a second connector comprising one or more contact pads, and a second conductive lead extending between the second electrode and the second connector to establish a path for conduction of an electrical signal between the second electrode and the second connector, and a sample chamber for receiving a sample, said first and second electrode being disposed to contact a sample within the sample chamber whereby an electrochemical signal is generated, wherein the first and second connectors extend from a common edge of the electrochemical test strip and have open space therebetween, and wherein the contact pad or pads of the second connector are between the contact pads of the first connector when viewed in the plane of the test strip.

14. The system of claim 13, wherein the test strip has a first major surface and an opposing second major surface, and wherein the contact pads of the first connector are exposed on the first major surface, and the contact pad or pads of the second connector are exposed on the second major surface.

15. The system of claim 14, wherein the second connector comprises two contact pads disposed side-by-side in the plane of the test strip, said two contacts pads not being in direct electrical contact with one another.

16. The system of claim 13, wherein the second connector comprises two contact pads disposed side-by-side in the plane of the test strip, said two contacts pads not being in direct electrical contact with one another.

17. The system of claim 13, wherein the test strip has a first major surface and an opposing second major surface, and wherein the contact pads of the first connector are exposed on the first major surface and on the second major surface, and the contact pad or pads of the second connector are exposed on the first major surface and the second major surface.

18. The system of claim 13, wherein the second connector comprises two contact pads disposed side-by-side in the plane of the test strip, said two contacts pads not being in direct electrical contact with one another.

19. The system of claim 13, wherein the contact pads of the first connector are separated by a non-conductive separation, and this non-conductive separation is extended through a portion of the lead connector.

20. The system of claim 19, wherein the second connector has two contact pads separated by a non-conductive separation, and this non-conductive separation is extended through a portion of the lead connector.

21. The system of claim 13, wherein the second connector has two contact pads separated by a separation, and this separation is extended through a portion of the lead connector.

22. The system of claim 13, further comprising a reagent for detection of an analyte disposed within the sample chamber.

23. The system of claim 22, wherein the reagent comprises an enzyme effective to oxidize glucose and a redox mediator, and the meter displays a measurement of glucose concentration.

* * * * *